(12) United States Patent
Wegener Tams et al.

(10) Patent No.: US 8,309,079 B2
(45) Date of Patent: Nov. 13, 2012

(54) USE OF FRUCTANASES IN FEED OF HOOFED ANIMALS, PREFERABLY TO PREVENT DISEASES

(75) Inventors: Jeppe Wegener Tams, Gentofte (DK); Petra Philipps, Grenzach-Wyhlen (DE)

(73) Assignee: DSM IP Assets B.V., Heerlen (NL)

( * ) Notice: Subject to any disclaimer, the term of this patent is extended or adjusted under 35 U.S.C. 154(b) by 712 days.

(21) Appl. No.: 12/089,557

(22) PCT Filed: Oct. 18, 2006

(86) PCT No.: PCT/EP2006/010039
§ 371 (c)(1),
(2), (4) Date: Jun. 6, 2008

(87) PCT Pub. No.: WO2007/045450
PCT Pub. Date: Apr. 26, 2007

(65) Prior Publication Data
US 2009/0252719 A1 Oct. 8, 2009

(30) Foreign Application Priority Data
Oct. 21, 2005 (EP) .................................. 05022984

(51) Int. Cl.
*A61K 38/47* (2006.01)
*C12N 9/24* (2006.01)
(52) U.S. Cl. ..................................... 424/94.61; 435/200
(58) Field of Classification Search .......................... None
See application file for complete search history.

(56) References Cited

U.S. PATENT DOCUMENTS
6,524,827 B2 * 2/2003 Moller et al. ................... 435/74
2002/0076790 A1 6/2002 Moller et al.

FOREIGN PATENT DOCUMENTS
WO 2006/100468 9/2006

OTHER PUBLICATIONS

Rozen et al FEMS microbiol let 2001, pp. 205-210.*
Walker et al carbohydrate res 1983, pp. 101-112, see abstract.*
Gern et al., "Screening for microorganisms that produce only endo-inulinase", *Applied Microbiology and Biotechnology*, vol. 55, No. 5, May 2001, pp. 625-635, XP002460873.
Zhengyu et al., "Production of inulooligosaccharides by endoinulinases from *Aspergillus ficcum*", *Applied Science.*, vol. 38, No. 3, Apr. 2005, pp. 301-308, XP004718879.
French et al., "Equine laminitis: loss of hemidesmosomes in hoof secondary epidermal lamellae correlates to dose in an oligofructose induction model: an ultrastructural study", *Equine Veterinary Journal*, vol. 36, No. 3, Apr. 2004, pp. 230-235, XP009093066.
Bailey et al., "Identification of equine cecal bacteria producing amines in an in vitro model of carbohydrate overload", *Applied and Environmental Microbiology*, vol. 69, No. 4, Apr. 2003, pp. 2087-2093, XP002386393.
Longland et al., "Pasture nonstructural carbohydrates and equine laminitis", *Journal of Nutrition*, vol. 136, No. 7, 2006, pp. 20995-21025, XP002460566.
International Search Report for PCT/EP2006/010039 mailed Dec. 28, 2007.

* cited by examiner

*Primary Examiner* — Tekchand Saidha
*Assistant Examiner* — Md. Younus Meah
(74) *Attorney, Agent, or Firm* — Nixon & Vanderhye, P.C.

(57) ABSTRACT

Laminitis is defined as an inflammation of the sensitive laminae of the hoof, especially in horses. It has been surprisingly found that fructanases such as 2,1-β-D-fructan hydrolase are highly effective as therapeutic and prophylactic agents against laminitis in horses. The fructanases may be used as enzyme compositions in horse feed, as additives for horse feed or as oral preparations for the therapy and prophylaxis of laminitis. Because of its effectiveness in hydrolyzing fructans, which seem to play an important role in the aetiology of laminitis, the administration of fructanases in combination with an increased intake of fructans or with an increased availability of fructans is particularly advantageous.

6 Claims, 1 Drawing Sheet

USE OF FRUCTANASES IN FEED OF HOOFED ANIMALS, PREFERABLY TO PREVENT DISEASES

This application is the U.S. national phase of International Application No. PCT/EP2006/010039 filed 18 Oct. 2006 which designated the U.S. and claims priority to European Patent Application No. 05022984.8 filed 21 Oct. 2005, the entire contents of each of which are hereby incorporated by reference.

The present invention improves the overall health of hoofed animals, and more specifically, treats and prevents laminitis.

Laminitis is defined as an inflammation of the sensitive laminae of the hoof, especially in horses. Laminitis is also defined as the inflammation of the laminae or fleshy plates along the coffin bone of a horse; and yet further defined as inflammation of the laminated tissue that attaches the hoof to the foot of a horse, which allows on a chronic stage the rotation of the coffin bone, also called founder.

Laminitis is a potentially devastating condition which can strike any hoofed animal, but is primarily known to affect equine. Generally speaking, laminitis is a syndrome involving the sensitive laminae of the hoof. The lamina is a layer of loose connective tissue attaching the distal phalanx to the hoof wall.

The syndrome can proceed through several stages, beginning with little or no visible signs of the disease, though lamellar damage may have already occurred at this point. Once begun, if unchecked, the condition can advance to a chronic stage, which can involve detachment of the lamina from the hoof and palmar rotation or even distal displacement of the bone. At the chronic stage, a horse can be left with continuous mild or severe pain which can last indefinitely. It is generally held that the laminitis syndrome is responsible for the permanent debilitation of countless horses every year, affecting all breeds around the world.

While the pathophysiology of the syndrome has gained understanding in recent years, attempts at treatment and prevention of the disease have met with limited success. In the past, treatment was limited to physical treatment of the affected foot, by, for example, minimizing movement by standing the horse in a deep (18 inch) bed of shavings, or fitting special frog supports for the animal. Chemical treatment of symptoms has also been utilized in the past, such as administration of phenylbutazone for inflammation and pain.

More recently, studies have shown that laminitis may begin as a primary vascular disease, and treatment methods have focused on vascular control mechanisms. For example, it has been proposed that digital venoconstriction may be the primary disturbance occurring in the initial stages of laminitis. As a result, certain substances have been examined that may interrupt this process. For example, certain catecholamine antagonists have been examined for possible efficacy. Success has been limited, however. For example, the [alpha]-adrenergic antagonist phenoxybenzamine has been associated with side effects such as hypotension, recumbency, and a prolonged duration of action. Similarly, when the [alpha]-adrenergic antagonist acepromazine maleate has been examined, undesirable side effects such as sedation and cholinesterase inhibition can occur in the animal.

Now, it has been surprisingly found that fructanases such as 2,1-β-D-fructan hydrolase are highly effective as therapeutic and prophylactic agents against laminitis in horses. The fructanases may be used as enzyme compositions in horse feed, as additives for horse feed or as oral preparations for the therapy and prophylaxis of laminitis. Because of its effectiveness in hydrolyzing fructans, which seem to play an important role in the aetiology of laminitis, the administration of fructanases in combination with an increased intake of fructans or with an increased availability of fructans is particularly advantageous. In the temperate forage grasses, the water soluble carbohydrates sucrose and fructan are the primary carbon reserves in the vegetative tissues. Recent studies show, that the fructan concentration in grass varies between May and August and that the hydrogen expiration after fructan intake indicates an intensive fermentation process in the small intestine of the animal.

Without being bound by any theory, the applicant believes that the basic damage of the laminar structure originates from an endo-toxin produced by intestinal microorganisms which mainly use fructan as carbon source. The applicant believes that the cleavage of fructan prevents an increased multiplying of the microorganism and disrupts the toxic molecule formation, that otherwise cause damage to the blood vessels that conform the laminae.

The fructanase used for treatment of the animal can be added to complete diets or complementary diets and/or can be administered directly to the animal by any suitable method. For example, the enzyme can be administered orally, for example in tableting form.

Lamellar damage due to laminitis is known to occur primarily in horses, but it can occur in any hoofed animal. The treatment of the present invention is therefore equally efficacious for other hoofed animals, such as, for example, cattle, camels, goats, pigs, and sheep.

It is therefore one of the main objects of the present invention to provide methods of preventing and treating laminitis in hoofed animals, e.g. horses; promoting healthy skin, hair, and hoof tissue, comprising administering to the animal an effective amount of a composition containing at least one fructanase for promoting healthy hoof tissue. More specifically, the invention relates to the use of fructanases as a medicament, preferably as a medicament for animals, especially for preventing or treating of laminitis in hoofed animals, i.e. to the use of at least one fructanase for the manufacture of a composition for the therapy and prophylaxis of laminitis in hoofed animals.

In another aspect, the present invention relates to a food and a food composition for hoofed animals such as horses, said food or food composition comprising at least one fructanase.

In a further aspect, the present invention relates to enzyme compositions for the preparation of diets or for the preparation of animal drugs, e.g. tablets for oral consumption. In a preferred embodiment, the enzyme composition is intended for being added to the drinking water of the hoofed animal.

In just another preferred embodiment the enzyme is expressed in a plant, preferably a fodder plant such as, e.g., a grass, which may ensure a more constant enzyme/substrate ratio, which is advantageous, at least in the case of grassing horses. Fructanases usable according to the invention may be obtained from microorganisms of any genus, for example from strains of *Paenibacillus, Streptococus* or *Aspergillus*.

As used herein, fructanases refer to enzymes which are able to decompose fructans such as inulin, levan, and sucrose. Examples of such enzymes are: fructan beta-fructosidases, which hydrolyze terminal, non-reducing 2,1- and 2,6-linked beta-D-fructofuranose residues in fructans; and inulinases, which are members of the group of glycoside hydrolases, which hydrolyze the internal 2,1-beta-D-fructosidic linkages of inulin to yield inulotriose, -tetraose, and -pentaose as the main products. In what follows, the designations "inulinase" and "endo-inulinase" are used interchangeably.

Fructanases are commercially available, e.g. the FRUCTOZYME® product from Novozymes A/S, Krogshoejvej 36, DK-2880 Bagsvaerd, Denmark.

In a preferred embodiment the fructanase is an enzyme classified as EC 3.2.1.80, the official name of which is fructan beta-fructosidase (alternative name exo-beta-D-fructosidase).

In another embodiment of the invention the fructanase is an enzyme classified as EC 3.2.1.7, the official name of which is inulinase (alternative name 2,1-Beta-D-fructan fructanohydrolase). The cloning of the endo-inulinase from *Aspergillus ficuum* ATCC 16882 is described in Uhm et al, Biotechnol. Lett. 20:809-812 (1998). The corresponding nucleic acid sequence and amino acid sequence of the *Aspergillus* ficuum endo-inulinase is shown in SEQ ID No:1 and SEQ ID No:2 respectively. In just another embodiment of the invention the fructanase has an amino acid sequence which has a degree of identity to the mature part of SEQ ID NO:2 of at least 80% and endo inulinase activity. The mature part of SEQ ID NO: 2 is expectedly amino acids 24-516 thereof.

In a particular aspect of the present invention, the at least one fructanase has a 2,6-beta-D-fructan or a 2,1-beta-D-fructan hydrolase activity.

2,6-β-D-fructans, such as levans of bacterial origin and phleins of plant origin, are substantially β-2,6-fructose polysaccharides consisting of a variable number of fructose units combined by β-(2-6)-glycosidic linkages.

In phlein, β-2,1 branching points also exist depending on the plant origin. Many plants, in particular grasses, store phlein as reserve polysaccharides in stems and leaves. As grasses are ubiquitous plants, phlein is an attractive resource as it is available in almost unlimited amounts.

2,6-β-D-fructan hydrolase activity as used herein is defined as the ability of an enzyme of hydrolyzing 2,6-β-D-fructo-furanosidic linkages in 2,6-β-D-fructans. A measure of 2,6-β-D-fructan hydrolase activity is a Levan Reducing sugar Unit (LRU), where 1 LRU is defined as the amount of enzyme that generates an amount of reducing groups in a levan substrate equivalent to 1 μmol fructose per minute.

In a preferred embodiment the fructanase usable according to the invention is further characterized by having one or more of the following properties:
a) a 2,6-β-D-fructan hydrolase or a 2,1-β-D-fructan hydrolase activity optimum in the pH range of 2.5-9.5, measured at 37° C.;
b) a 2,6-β-D-fructan hydrolase or a 2,1-β-D-fructan hydrolase activity optimum in the temperature range of 20-70° C., measured at a pH in the range of 4-6, such as pH 4.0, pH 5.0 or pH 6.0, preferably at pH 4.0,
d) pepsin stability.

A preferred pH-activity optimum range is from about 2.5 to about 8.5. A more preferred pH-activity optimum range is from about 3 to 6

The food and food composition for hoofed animals according to the present invention may be based on any conventional food for such animals, for example horse food. There is a wide range of horse foods available which may be grouped into (a) complete diets, (b) complementary diets, and (c) snacks and treats. Complete diets may be fed for an extended period as the sole source of nutrients and will provide for all the energetic and nutrient needs of the animal and the physiological state for which it is intended. Complementary diets normally are not sufficient to ensure that all nutrient and energy requirements are met unless fed in combination with another foodstuff, for example grass or drinking water. Snacks and treats are for occasional feeding and are considered as complementary products. The horse food of the present invention may be in a dry, canned, semi-moist or baked form. Typical components of such compositions, in addition to Inventive Ingredients, are crude protein, crude fat, carbohydrates, starch, crude fibers, and ash, further on minerals, trace elements, vitamins, fatty acids, protein and amino acids, choline, carnitin, dietary fiber and substances required for balanced diets of the different animal species.

Basic ingredients of such food compositions are
Crude Protein including proteins and N-containing compounds of non-proteinaceous nature, e.g. acid amides, amines, free amino acids, ammonium salts, alkaloids;
Crude Fat including neutral fats, lipoids (phospho-, sphingolipids, steroids) and other ethersoluble compounds;
N-free Extractions (NFE) including polysaccharides (starch, glycogen), soluble saccharides (glucose, fructose, saccharose, lactose, maltose and oligosaccharides), and soluble fractions of cellulose, hemicellulose, lignin and pectins;
Crude Fibers including insoluble fractions of cellulose, hemicellulose, lignin and other components of the cell wall like suberin, cutin etc.;
Ash including minerals (macrominerals such as calcium, phosphorus, sodium, chloride, potassium, magnesium, and microminerals, i.e., trace elements, such as iron, copper manganese, zinc, iodine, selenium,) and further inorganic substances e.g. silicate.
Vitamins including vitamins A, $B_1$, $B_2$, $B_6$, $B_{12}$, D, pantothenic acid, niacin, biotin, folic acid, linolic acid and choline.

Further components may, e.g. be omega-6-fatty acids, omega-3-fatty acids, L-carnitine, chondroitin sulfate, glucosamine, glutamine/glutamic acid, arginine, taurine and hydroxyproline.

The enzyme composition according to the present invention may be based on any conventional enzyme composition. It comprises the at least one fructanase and additionally for stabilizing the composition sugar carbohydrates and/or potassium sorbate and/or sodium chloride.

In regard to the animal drug for oral consumption, the enzyme composition comprises a 2,6-β-D-fructan and/or a 2,1-β-D-fructan hydrolase, preferably purified and essentially free of any active contaminants.

Dependent on the form of the composition for oral consumption, additional products may be present, e.g. sugar carbohydrates, silica, starch, alginates, pectin, and cellulose derivatives, such as hydroxyethyl cellulose, sodium carboxymethyl cellulose and hydroxypropyl cellulose, polyacrylic acid and its salts.

The 2,6-β-D-fructan hydrolase and/or the 2,1-β-D-fructan hydrolase of the invention should be dosed in amounts sufficient for achieving the desired degree of hydrolysis within the desired reaction time. It is at present contemplated that a suitable enzyme dosage (gram of enzyme protein per gram of feed) is in the range of from 1 ppm (parts per million) to 1%, preferably from 5 ppm to 1%, from 10 ppm to 1%, from 10 ppm to 0.5%, most preferably from 50 ppm to 0.5%. As mentioned above, the present invention is generally directed to treatment of laminitis in hoofed animals. The treatment can be either prophylactic or therapeutically after physical manifestations of the disease have appeared.

The effect of fructanases will now be illustrated in more detail by the following experimental results. These results are described with reference to the drawing. In the drawing the FIGS. 1 and 2 show a graph representing in vitro experiments which demonstrate that a purified fructanase from *Aspergillus* is able to degrade fructans under conditions relevant for the digestive tract of hoofed animals.

EXAMPLE 1

Figure 1:
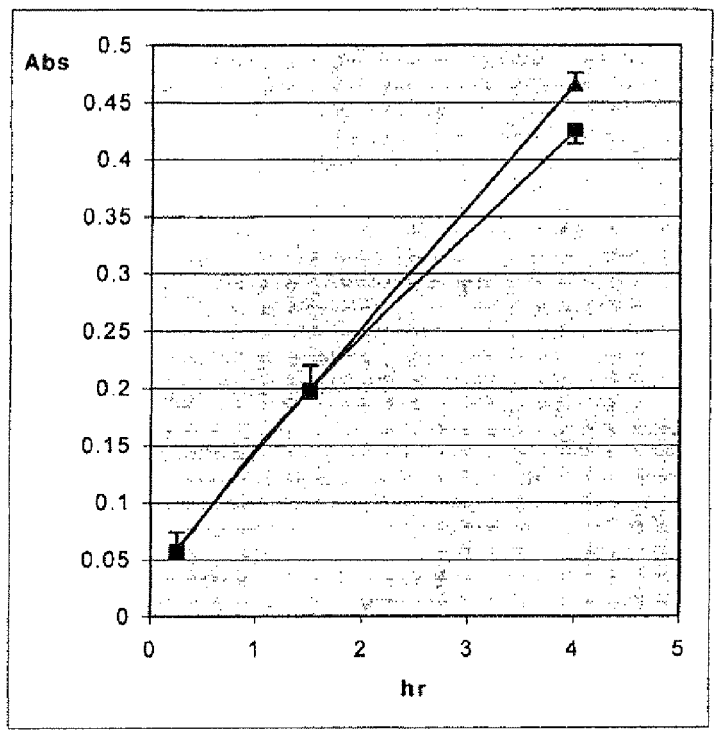
FIG. 1 depicts the fructanase activity (triangle) without pepsin and (solid box) in the presence of pepsin and relates to Example 2.

Fermentation and Purification of Endo-Inulinase from *Aspergillus niger*

Fermentation

A strain of *Aspergillus niger* such as the strain available from DSMZ, Deutsche Sammlung von Mikroorganismen und Zellkulturen GmbH, Braunschweig, Germany with DSM no. 737 is fermented using standard methods, and the fermentation liquor is centrifuged, filtered to remove remaining cell debris and the like, if any, of the production organism, and concentrated by ultrafiltration, all using standard methods.

The *Aspergillus niger* endo-inulinase prepared has an amino acid sequence similar to SEQ ID No2, is encoded by a nucleotide sequence similar to SEQ ID No. 1 and can therefore also be prepared by recombinant methods, as generally described by Uhm et al].

Purification

The ultrafiltrated fermentation supernatant from *A. niger* described above was transferred to 20 mM HEPES/NaOH, pH 7 on a G25 sephadex column and applied to a Q-sepharose FF column equilibrated in 20 mM HEPES/NaOH, pH 7. After washing the column extensively with the equilibration buffer, the endo-inulinase protein was eluted with a linear NaCl gradient (0—>0.5M) in the same buffer. Fractions, collected during elution, were analysed by SDS-PAGE and for endo-inulinase activity. Endo-inulinase containing fractions were pooled and solid ammonium sulfate was added to the pool to give a 1.6M final $(NH_4)_2SO_4$ concentration in the solution. The solution was mixed gently with a magnetic stirrer during the $(NH4)_2SO4$ addition and the stirring was continued for 30 minutes after the addition to bring the system in equilibrium. Then the enzyme solution was applied to a Phenyl Toyopearl column equilibrated in 20 mM succinic acid/NaOH, 1.6M $(NH_4)_2SO_4$, pH 6. After washing the column extensively with the equilibration buffer, the endo-inulinase was eluted with a linear $(NH_4)_2SO_4$ gradient (1.6—>0M) in the same buffer. Endo-inulinase containing fractions were analysed by SDS-PAGE analysis and fractions, where only one band was seen on the coomassie stained SDS-PAGE gel, where pooled and transferred to 20 mM succinic acid/NaOH, pH 6 by dialysis. The dialysed enzyme was the purified endo-inulinase.

The purified endo-inulinase has a pH-optimum at 37° C. of between pH 4-5, a temperature optimum at pH 4 of between 50 and 60° C., and more than 80% residual activity at pH 4-8 after 2 hours' incubation at 37° C., all determined using the Azo-Fructan assay described below.

Endo-inulinase assay

Substrate Azo-fructan (azo-dyed high molecular weight fraction of chicory fructan; from Megazyme)
Temperature: 37° C.
Assay buffer: 100 mM succinic acid/NaOH, 0.01% Triton X-100, pH 5.0.
Stop reagent: 10 ml 2M KOH+100 ml 96% ethanol.

2% (w/v) Azo-fructan was suspended in 0.01% Triton X-100 by gentle stirring. 120 µl of this suspension and 120 µl Assay buffer were mixed in an Eppendorf tube and placed on ice. 40 µl endo-inulinase sample (diluted in 0.01% Triton X-100) was added. The assay was initiated by transferring the Eppendorf tube to an Eppendorf thermomixer, which was set to the assay temperature. The tube was incubated for 30 minutes on the Eppendorf thermomixer at its highest shaking rate (1400 rpm). The incubation was stopped by transferring the tube back to the ice bath and adding 1000 µl Stop reagent. Then the tube was allowed to reach room temperature, centrifuged (25° C., 10 min, 1000×g) and 200 µl supernatant was transferred to a microtiter plate. OD590 was read as a measure of endo-inulinase activity. A buffer blind was included in the assay (instead of enzyme).

EXAMPLES 2 TO 4

In Vitro Testing of Fructanase Under Relevant Conditions

Figure 2:
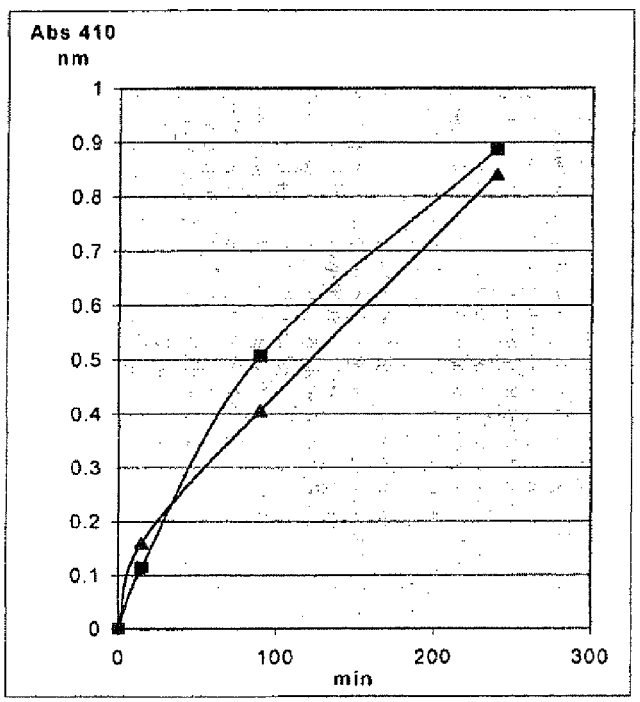
FIG. 2 depicts the fructanase digestion of levan using reducing sugar assay (triangle) without pepsin and (solid box) in the presence of pepsin and relates to Example 3.

To demonstrate that the purified fructanase from *Aspergillus* is able to degrade fructans, relevant to grass, under conditions relevant for the digestive tract of horses, the effect of the purified enzyme was tested in vitro at pH 3.5 and 37° C. for up to 4 hours. To test the pepsin stability of the enzyme, similar testing was carried out in the presence of pepsin. FIG. 1 related to example 2 shows the fructanase activity (▲) without pepsin and (■) in the presence of pepsin. FIG. 2 related to example 3 shows the fructanase digestion of levan using reducing sugar assay (▲) without pepsin and (■) in the presence of pepsin

EXAMPLE 2

Substrate: Azo-Fructan (S-AZFR540, Megazyme)
Assay conditions: pH 3.5 and 37° C. for up to 4 hours
Azo-fructan assay:

240 µl 1% (w/v) Azo-Fructan (S-AZFR540, Megazyme), 50 mM sodium malate buffer pH 3.5. The reaction was initiated by adding 47 µl 0.06 mg/ml endo-inulinase solution, purified according to Example 1, with or without 100 mg/l pepsin (Sigma) and incubated 0.25, 1.5 and 4 hours at 37° C. and stopped by adding 1 ml 1M KOH, 50% EtOH. The suspensions were centrifuged for 3 min at 5000 g and 200 µl supernatant were transferred to micro titer plates, and the absorbance at 590 nm was measured, using Spectra Max 190, Molecular Dynamics. The enzyme effect was calculated as the difference between the absorbance of an enzyme sample and the absorbance of a control sample without enzyme.

The results of Example 2 are shown in Tab. 1 and FIG. 1.

TABLE 1

| Time (h) | without pepsin | STDEV | with pepsin | STDEV |
|---|---|---|---|---|
| 0.25 | 0.059 | 0.015 | 0.058 | 0.006 |
| 1.5 | 0.199 | 0.021 | 0.199 | 0.008 |
| 4 | 0.466 | 0.010 | 0.425 | 0.011 |

EXAMPLE 3

Substrate: Levan from *erwinia herbicola*, Sigma
Assay conditions: pH 3.5 and 37° C. for up to 250 minutes
Reducing sugar assay (PAHBAH):

The enzyme reaction was initiated by adding 100 µl 0.12 mg/ml endo-inulinase solution, purified according to Example 1] to 200 µl 3% (w/v) levan (from *erwinia herbicola*, Sigma), 50 mM sodium malate buffer pH 3.5 in PCR tubes. This solution was incubated for 0, 15, 90 and 240 minutes at 37° C. in a Peltier Thermal Cycler (PCT-200, MJ research) and transferred to 450 µl stop solution, 1.5% (w/v) p-hydroxybenzoic acid hydrazide, for short PAHBAH (Sigma, H-9882), 5% (w/v) K-Na-tartrate (Merck, 1.08087), 2% (w/v) NaOH and incubated at 95° C. for 10 min. The temperature was lowered to 20° C. and 150 µl is transferred to a 96 well micro titter plate, the absorbance was then measured at 410 nm with a microplate reader (Spectra Max 190, Molecular Devices). Enzyme effect was calculated as the difference between the absorbance of an enzyme sample and the absorbance of a control sample without enzyme.

The results of Example 2 are shown in Tab. 2 and FIG. 2.

TABLE 2

| Time (minutes) | without pepsin | with pepsin |
|---|---|---|
| 0 | 0 | 0 |
| 15 | 0.160 | 0.114 |
| 90 | 0.406 | 0.507 |
| 240 | 0.841 | 0.887 |

Results

The two examples show significant effect on fructan at the applied conditions, and both examples show that the enzyme is compatible with pepsin under the conditions given.

EXAMPLE 4

To demonstrate that the purified fructanase from *Aspergillus* is capable of hydrolysing fructans from a commonly used foddergrass an extract of ryegrass was prepared and incubated with the enzyme under standard assay conditions, as described in detail below.

Fructans were extracted from a lyophilised and pulverised sample of field-grown ryegrass (*Lolium perenne*) containing both stem and leaf material, by consecutive extractions with first ethanol (2 times with 80% ethanol at 80° C. for 1 hour) then with water (2 times at 60° C. for 1 hour) as described in "H Smouter and R J Simpson, Occurrence of fructans in the Graminaea (Poaceae), New Phytologist vol. 111 pp. 359-368, 1989" with the exception that only the aqueous supernatants were combined to minimise the presence of free sugars in the extract.

For assaying fructanase activity 90 µl of the fructan extract described above at a concentration of approximately 0.2% (w/v) in 50 mM acetate buffer pH 5.0 was combined with 10 µl of different dilutions of an endo-inulinase solution prepared according to example 1. After incubation for 1 hour at 37° C. the enzyme reaction was stopped by addition of 900 µl 160 mM Carbonate/bicarbonate buffer at pH 10 and a 100 µl aliquot was incubated with 50 µl PHBAH reagent (0.5 N NaOH, 0.177 M K,Na tartrate, 5 mM bismuth acetate and 0.1 M p-hydroxybenzoic acid hydrazide) at 95° C. for 10 min. Subsequently 50 µl was transferred to a microtiterplate containing 50 µl PHBAH buffer (0.5 N NaOH, 0.177 M K,Na tartrate and 5 mM bismuth acetate) and absorbance at 405 nm was measured with a microplate reader (Infinite series, Tecan).

The enzyme effect was calculated as the difference between an enzyme containing sample and a control sample without enzyme (blank). Prior to this calculation, the background absorbance of a water sample containing no reducing ends was subtracted from all measurements.

The results of the described experiment are shown in table 3

TABLE 3

| Hydrolysing activity of purified *Aspergillus* endo-inulinase on ryegrass fructan. | | |
|---|---|---|
| Enzyme dilution factor | OD405 | % of blank |
| 1 | 0.2859 | 211 |
| 10 | 0.1575 | 116 |
| 100 | 0.1445 | 107 |
| blank | 0.1356 | 100 |

The results in table 3 clearly demonstrate that the purified endo-inulinase or fructanase enzyme from *Aspergillus* can degrade fructans from a fodder grass.

The invention claimed is:

1. A method for decreasing growth of bacteria fed on fructose in a hoofed animal with fructanase comprising the step of administering an effective amount of at least one fructanase to said animal, wherein said at least one fructanase is an endo-inulinase comprising the amino acid sequence of SEQ ID NO:2.

2. The method of claim 1 wherein the at least one fructanase has a 2,1-β-D-fructan hydrolase activity.

3. The method of claim 1 wherein the at least one fructanase has a 2,6-β-D-fructan hydrolase activity.

4. The method of claim 3 wherein the at least one fructanase comprises one or more of the following properties:

a) a 2,6-β-D-fructan hydrolase activity optimum in the pH range of 2.5-9.5, measured at 37° C.;

b) a 2,1-β-D-fructan hydrolase activity optimum in the pH range of 2.5-9.5, measured at 37° C.;

c) a 2,6-β-D-fructan hydrolase;

d) a 2,1-β-D-fructan hydrolase activity optimum in the temperature range of 20-70° C.; and e) pepsin stability.

5. The method of claim 4 wherein the fructanase is characterized by having a 2,6-β-D-fructan hydrolase activity optimum in the pH range of 3-6, measured at 37° C.

6. The method of claim 4 wherein the fructanase is characterized by having a 2,1-β-D-fructan hydrolase activity optimum in the pH range of 3-6, measured at 37° C.

* * * * *

SEQUENCE LISTING

<160> NUMBER OF SEQ ID NOS: 4

<210> SEQ ID NO 1
<211> LENGTH: 942
<212> TYPE: DNA
<213> ORGANISM: Gluconobacter oxydans DSM 17078

<400> SEQUENCE: 1

```
atgaaaacgg catttgcttt tgccgcaatg ctgacggctg cgccatttct ggcgccgctt      60
gcagcaggtc aggcccatgc agcggataac agcgcacccc tgcgcttcgt gctgatcccc     120
aagaccgtgc atccctggtt cgacaaggcg aataacggag cacaggcggc tgcagcaatg     180
atctcgcagg cgacggggcg gaaggtcgag atcgaatacc gcgcgccgca gacggcggat     240
gtgtcgtccc agaacgacat catcgagcgt gccatcgcga cccatccgga cgggctgatt     300
ctcgacctgc tggacgagaa gggcaaccgc gcgaccatgg acgaggcggt ggacgagaag     360
atccccatga cggtgtttga ttccctgccg cccgaaggca tggagatcac ggccgtgggc     420
gcggatttct gcgagcaggg cacgatgcg ccgagcggc tggcgaacct ggtcggaaag     480
aagggcgaag tggcgatcat gatggggtg ccgacagcgc cgaaccatac gctgcgggcc     540
```

-continued

```
gagtgtgaaa agaaggtctt tgccaaatac ccggacatga aggttgtcgc gaccggcgtg    600
gacaatgaca gcatcgagac cgcccagaag caggcctctg ccatcatgca ggcacatccg    660
gatctggtcg gatgggttga gtgcgatgcc tcgggaccgg tgggcgtcgg ccaggccatc    720
cgcgagagcg gcaagacggg caaggtcaag gaagtgggc tcgataacct caacgacatg      780
atccagctca tcaaggatgg cgttgctgag tcctctgcgt cgagccggcc ggaaatgcag    840
ggttactggg ccgtcgtgtc tgcctggcag cgggcgatgg ggcagaagac gcccaaatac    900
atcgataccg gcatcgatct tctgacgagc aagaacctct ga                       942
```

```
<210> SEQ ID NO 2
<211> LENGTH: 313
<212> TYPE: PRT
<213> ORGANISM: Gluconobacter oxydans DSM 17078

<400> SEQUENCE: 2

Met Lys Thr Ala Phe Ala Phe Ala Ala Met Leu Thr Ala Ala Pro Phe
1               5                   10                  15

Leu Ala Pro Leu Ala Ala Gly Gln Ala His Ala Ala Asp Asn Ser Ala
            20                  25                  30

Pro Leu Arg Phe Val Leu Ile Pro Lys Thr Val His Pro Trp Phe Asp
        35                  40                  45

Lys Ala Asn Asn Gly Ala Gln Ala Ala Ala Met Ile Ser Gln Ala
    50                  55                  60

Thr Gly Arg Lys Val Glu Ile Glu Tyr Arg Ala Pro Gln Thr Ala Asp
65                  70                  75                  80

Val Ser Ser Gln Asn Asp Ile Ile Glu Arg Ala Ile Ala Thr His Pro
                85                  90                  95

Asp Gly Leu Ile Leu Asp Leu Leu Asp Glu Lys Gly Asn Arg Ala Thr
            100                 105                 110

Met Asp Glu Ala Val Asp Glu Lys Ile Pro Met Thr Val Phe Asp Ser
        115                 120                 125

Leu Pro Pro Glu Gly Met Glu Ile Thr Ala Val Gly Ala Asp Phe Cys
    130                 135                 140

Glu Gln Gly Thr Met Ala Ala Glu Arg Leu Ala Asn Leu Val Gly Lys
145                 150                 155                 160

Lys Gly Glu Val Ala Ile Met Met Gly Val Pro Thr Ala Pro Asn His
                165                 170                 175

Thr Leu Arg Ala Glu Cys Glu Lys Lys Val Phe Ala Lys Tyr Pro Asp
            180                 185                 190

Met Lys Val Val Ala Thr Gly Val Asp Asn Asp Ser Ile Glu Thr Ala
        195                 200                 205

Gln Lys Gln Ala Ser Ala Ile Met Gln Ala His Pro Asp Leu Val Gly
    210                 215                 220

Trp Val Glu Cys Asp Ala Ser Gly Pro Val Gly Val Gly Gln Ala Ile
225                 230                 235                 240

Arg Glu Ser Gly Lys Thr Gly Lys Val Lys Glu Val Gly Leu Asp Asn
                245                 250                 255

Leu Asn Asp Met Ile Gln Leu Ile Lys Asp Gly Val Ala Glu Ser Ser
            260                 265                 270

Ala Ser Ser Arg Pro Glu Met Gln Gly Tyr Trp Ala Val Val Ser Ala
        275                 280                 285

Trp Gln Arg Ala Met Gly Gln Lys Thr Pro Lys Tyr Ile Asp Thr Gly
    290                 295                 300
```

```
Ile Asp Leu Leu Thr Ser Lys Asn Leu
305                 310

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgaaaacgg catttgcttt                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tcagaggttc ttgctcgtca                                               20
```